(12) United States Patent
Eveland

(10) Patent No.: US 11,872,010 B2
(45) Date of Patent: Jan. 16, 2024

(54) CONTROLLING ACCESS TO A MEDICAL MONITORING SYSTEM

(71) Applicant: BRAEMAR MANUFACTURING, LLC, Eagan, MN (US)

(72) Inventor: Doug C. Eveland, Bonsall, CA (US)

(73) Assignee: Braemar Manufacturing LLC, Eagan, MN (US)

( * ) Notice: Subject to any disclaimer, the term of this patent is extended or adjusted under 35 U.S.C. 154(b) by 350 days.

(21) Appl. No.: 16/566,501

(22) Filed: Sep. 10, 2019

(65) Prior Publication Data
US 2020/0138289 A1     May 7, 2020

Related U.S. Application Data

(63) Continuation of application No. 11/004,311, filed on Dec. 2, 2004, now abandoned, which is a continuation-in-part of application No. 10/728,631, filed on Dec. 5, 2003, now Pat. No. 7,002,468, which is a continuation-in-part of application No. 09/841,154, filed on Apr. 23, 2001, now Pat. No. 6,664,893.

(51) Int. Cl.
*A61B 5/00*     (2006.01)
*G16H 10/20*     (2018.01)
*G16H 20/10*     (2018.01)
*G16H 40/67*     (2018.01)

(52) U.S. Cl.
CPC .......... *A61B 5/0006* (2013.01); *G16H 10/20* (2018.01); *G16H 20/10* (2018.01); *G16H 40/67* (2018.01)

(58) Field of Classification Search
None
See application file for complete search history.

(56) References Cited

U.S. PATENT DOCUMENTS 5,827,180 A * 10/1998 Goodman ............. A61J 7/0481
                                                        600/300
2001/0051787 A1 * 12/2001 Haller .................... G16H 40/67
                                                       705/2

* cited by examiner

*Primary Examiner* — Michael W Kahelin

(57) ABSTRACT

Systems and techniques for remote medical monitoring. In one implementation, a method includes monitoring a first medical condition of an individual, the monitoring being initiated remotely by a monitoring service, receiving a query relating to a second medical condition of the individual, transmitting a response to the query to the monitoring service, receiving a prompt from the monitoring service, and transmitting a response to the prompt to the monitoring service. The query is received from the monitoring service. The prompt is designed to provoke a particular action.

12 Claims, 8 Drawing Sheets

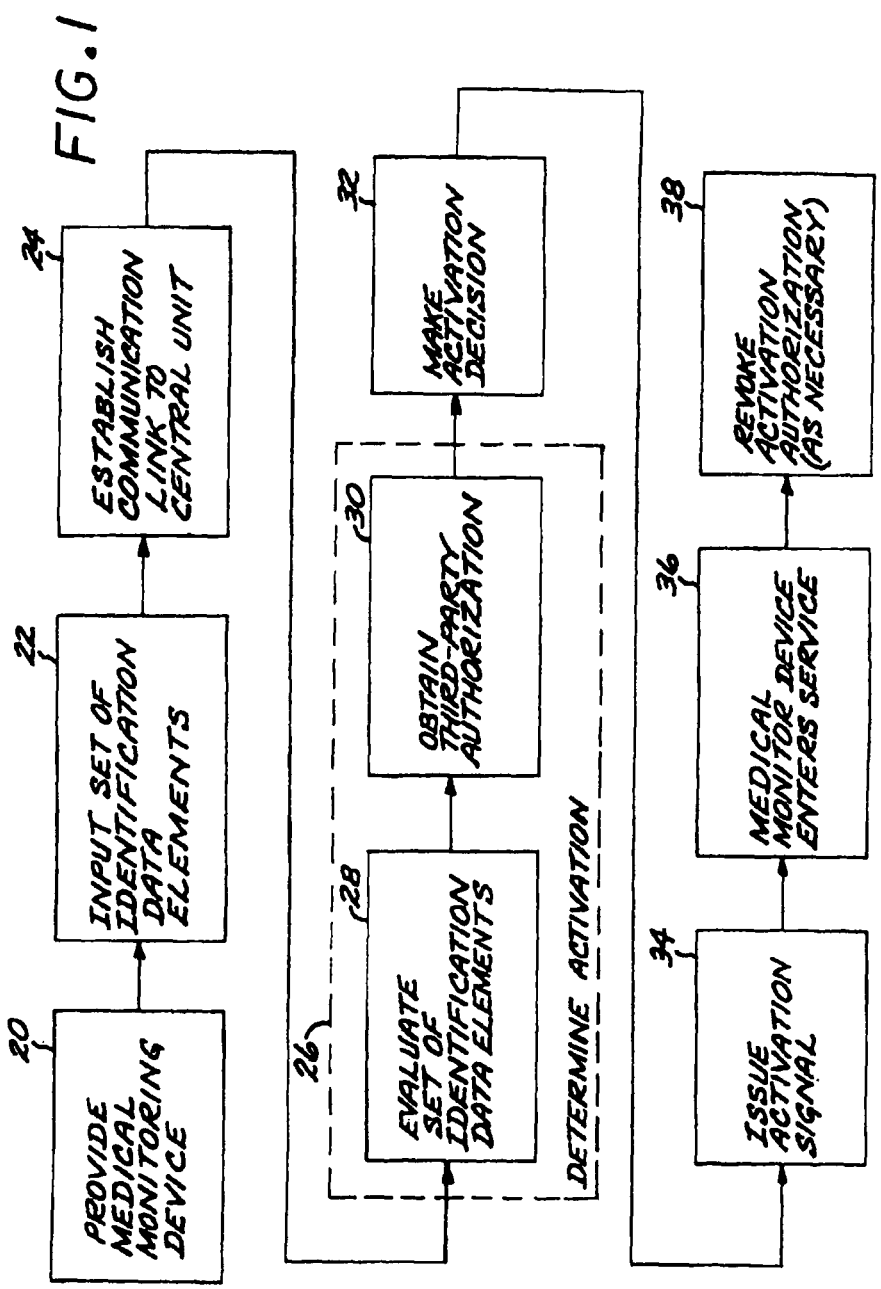

US 11,872,010 B2

CONTROLLING ACCESS TO A MEDICAL MONITORING SYSTEM

CROSS-REFERENCE TO RELATED APPLICATION

This application in a continuation-in-part of, and claims the priority to, U.S. application Ser. No. 10/728,631, filed Dec. 5, 2003, entitled CONTROLLING ACCESS TO A MEDICAL MONITORING SYSTEM, and published as U.S. Patent Publication No. 2004/0085186A1, which is a continuation-in-part of U.S. application Ser. No. 09/841,154, filed Apr. 23, 2001, now U.S. Pat. No. 6,664,893, the disclosures of both of which are hereby incorporated by reference.

BACKGROUND

The following description relates to controlling access to a medical monitoring device and/or a service associated with the device, for example, to help ensure that access to the monitoring device and service is authorized prior to commencing usage.

Advances in sensor technology, electronics, and communications have made it possible for physiological characteristics of patients to be monitored even when the patients are ambulatory and not in continuous, direct contact with, a hospital monitoring system. For example, U.S. Pat. No. 5,959,529 describes a monitoring system in which the patient carries a remote monitoring unit with associated physiological sensors. The remote monitoring unit conducts a continuous monitoring of one or more physiological characteristics of the patient according to the medical problem of the patient, such as the patient's heartbeat and its waveform.

One potential issue associated with the use of such medical monitoring devices is establishing whether the patient's health-care-benefit payer has authorized the use of the monitoring device and service. In the absence of a proper authorization, the patient may use the medical monitoring device and incur significant charges, for example, in the form of rental value of the medical monitoring device, telephone charges, charges at the central monitoring system, and charges by medical personnel, and the providers of those goods and services may not get paid. Bad debts—an increasing concern in the medical field generally—tend to be an even greater concern in the case of a portable medical monitoring device and its service where the physical control of the device is in the hands of a third party, such as a prescribing doctor, who does not own the medical monitoring device and is not responsible for improper charges.

SUMMARY

The present inventors recognized a need for controlling access to medical monitoring devices and their associated services to help ensure that only properly authorized patients can use the service. Controlling access to a medical monitoring system may be accomplished by a system and/or technique that includes one or more of the following features.

To control access to a medical monitoring system, a computer-based method may involve receiving information indicating that a remote monitoring device (e.g., a patient-portable device configured to monitor one or more physiological aspects of a patient) seeks access (e.g., through one or more communications links including either or both of a wired communication link and a wireless communication link) to a monitoring service hosted by a central unit, and determining whether the remote monitoring device is authorized to access the monitoring service. This determination is based at least in part on authorization data received from a third-party source. Based on a result of the determination, an activation signal is selectively issued to the remote monitoring device.

The determination of whether the remote monitoring device is authorized to access the monitoring service may be performed cooperatively between the remote device and the central unit. Further, the determination of whether the remote monitoring device is authorized to access the monitoring service may include one or both of (i) performing a format check on access data entered into the remote monitoring device and (ii) comparing the entered access data against the third-party authorization data.

The access control method may further include maintaining, at the central unit, a local database of third-party authorization data to be used in the determination of whether the remote monitoring device is authorized to access the monitoring service. The local authorization database may be updated, for example, periodically or based on a predetermined event or a combination of both.

Selectively issuing the activation signal to the remote monitoring device based on a result of the determination may include issuing the activation signal if the remote monitoring device is determined to be authorized to access the medical monitoring service and refraining from issuing an activation signal if the remote monitoring device is determined to be unauthorized to access the medical monitoring service.

In another aspect, a medical monitoring system centered at a central node includes one or more communications links configured to facilitate communications with remote monitoring devices (e.g., a patient-portable device configured to monitor one or more physiological aspects of a patient) and one or more third-party authorization sources. The medical monitoring system also includes at least one programmable processor configured to perform various operations. These operations may include hosting a medical monitoring service (e.g., implemented at least in part by one or more software processes), receiving information indicating that a remote monitoring device seeks access to the medical monitoring service hosted by a central unit, determining, based at least in part on authorization data received from a third-party authorization source, whether the remote monitoring device is authorized to access the monitoring service, and based on a result of the determination, selectively issuing an activation signal to the remote monitoring device.

The programmable processor may further be configured to maintain at the central node a local database of third-party authorization data to be used in the determination of whether the remote monitoring device is authorized to access the monitoring service. The local authorization database may be updated based on data received from the one or more third-party authorization sources. Updating may occur periodically or based on a predetermined event or a combination of both.

The programmable processor may further be configured to determine whether the remote monitoring device is authorized to access the monitoring service by one or both of (i) performing a format check on access data entered into the remote monitoring device and (ii) comparing the entered access data against the third-party authorization data.

The programmable processor may be configured to issue the activation signal to the remote monitoring device if the remote monitoring device is determined to be authorized to access the medical monitoring service and to refrain from issuing an activation signal if the remote monitoring device is determined to be unauthorized to access the medical monitoring service.

In another aspect, a portable medical monitoring device includes a transceiver for communicating with a central node, a user interface for communicating with a user of the device, and a programmable processor configured to perform various operations. These operations may include receiving user input specifying user-specific information, transmitting the received user input to the central node for third-party authorization based at least in part on the user-specific information, and selectively providing the user with access to a monitoring service hosted at the central node based on a result of the third-party authorization.

The programmable processor further may be configured to perform a format check on the received user input to determine whether the user input meets one or more predetermined criteria. If the user input is determined not to meet one or more of the predetermined criteria, the programmable processor may refrain from transmitting the received user input to the central station and/or may deny access to the monitoring service. In addition, the programmable processor may be configured to provide access to the monitoring service if the device receives an activation signal from the central node and to deny access to the monitoring service if the device fails to receive an activation signal from the central node.

Among other potential advantages, the systems and techniques described here may facilitate controlling access to medical monitoring devices and associated services. The approach may help to ensure that the term of service is initiated and continued only for persons who are properly authorized to have the service. For example, the present approach may activate the medical monitoring device and its corresponding service only for a person who provides proper identification data and is financially and otherwise properly authorized for the service. As a result, the chances of a wrong person being monitored may tend to be reduced. The activation process, which may involve the input of proper identification data, may be quick and largely transparent to the person seeking the service.

The systems and techniques described here may help to ensure that medical monitoring device services are provided only to properly identified and authorized persons. They may also help to ensure that all persons and agencies responsible for the medical monitoring device and the services are coordinated in their approval of rendering service to the particular patient and in effect have approved the provision of service and the type of service to be provided. Potential legal and financial liability may thereby be reduced.

In another aspect, a method includes monitoring a first medical condition of an individual, receiving, from the monitoring service, a query relating to a second medical condition of the individual, transmitting a response to the query to the monitoring service, and receiving a prompt from the monitoring service, the prompt designed to provoke a predetermined action. The monitoring can be initiated remotely by a monitoring service.

This and other aspects can include one or more of the following features. A response to the prompt can be transmitted to the monitoring service. The received prompt can be designed to provoke the monitored individual to undertake the predetermined action. The query can be, e.g., a blood glucose query inquiring as to a blood glucose concentration of the individual, a blood pressure query inquiring as to a blood pressure of the individual, or a weight query inquiring as to a weight of the individual.

The prompt received from the monitoring service can be, for example, a medication prompt designed to provoke the monitored individual to medicate, a sample prompt designed to provoke the collection of a sample, an electrode check prompt designed to move the monitored individual to check an electrode, or a communications check prompt designed to move the monitored individual to ensure that communications with the monitoring service are maintained. The prompt can also be a battery check prompt designed to move the monitored individual to check a charge on the battery, a physical activity prompt designed to move the monitored individual to curtail or halt physical activity, or a prompt designed to move the monitored individual to lie down or sit down.

The can also include receiving input from the monitored individual and using the input in responding to the query. Monitoring the first medical condition can include monitoring cardiac function of the individual.

In another aspect, a machine-readable medium can store instructions operable to cause one or more devices to perform operations. The operations can include monitoring a medical condition of an individual, transmitting a result of the monitoring to a monitoring service, receiving an activity prompt from the monitoring service, prompting the activity related in the activity prompt, and transmitting a response to the prompt to the monitoring service. The activity prompt can relate an activity that is to be prompted.

This and other aspects can include one or more of the following features. The activity can be prompted by relaying the prompt to the monitored individual and receiving a response to the relayed prompt from the monitored individual. The prompted activity can be the collection of a sample. For example, the collection of the result of the monitoring can be provoked or the monitored individual can be provoke to medicate with a specific medication. For example, the monitored individual can be provoked to medicate using a pharmaceutical composition having a specific color.

The operations can also include receiving a query from the monitoring service. The query can relate to a second medical condition of the individual. The operations can also include receiving adapted parameters for the monitoring of the medical condition of the individual, and adapting the monitoring of the medical condition in accordance with the received parameters. The response can be transmitted without input from the monitored individual.

In another aspect, a method includes receiving a monitoring result from a remote monitoring device, receiving, from the remote monitoring device, a response to one or more of a prompt to provoke a specific action and a query regarding a second medical condition of the individual; and adapting the monitoring of the first medical condition of the individual by the remote monitoring device based on the received response. The remote monitoring device remotely monitors a first medical condition of an individual.

This and other aspects can include one or more of the following features. Receiving the response can include receiving a response to one or more of an individual-specific prompt and an individual-specific query tailored to the monitored individual. The monitoring result and the response can be stored. To adapt the monitoring, adapted monitoring parameters can be transmitted to the remote monitoring device. For example, adapted parameters for the identification of cardiac states can be transmitted to the remote monitoring device.

In another aspect, a method of conducting a clinical trial includes remotely prompting an individual to medicate in accordance with a regimen of the clinical trial and remotely monitoring a cardiac function of the individual during the medication over a remote electrocardiographic monitoring device.

This and other aspects can include one or more of the following features. A response to the prompt indicating that the individual has indeed medicated in accordance with the clinical trial can be received. The individual can be prompted to take a specific pharmaceutical composition, and the efficacy or safety of the prompted medication can be determined. The individual can be remotely prompted over the remote electrocardiographic monitoring device.

In another aspect, a method performed at a central monitoring system includes receiving, from a remote sensing device, information related to a medical condition of a monitored individual associated with the remote sensing device and, based at least in part on the received information, transmitting, to the remote sensing device, information designed to instruct the monitored individual.

This and other aspects can include one or more of the following features. The information designed to instruct the monitored individual can include instructions to undertake a predetermined action. For example, the instructions to undertake a predetermined action can include transmitting instructions to take medicine, transmitting instructions to contact a doctor, transmitting instructions to sit down, transmitting instructions to reduce altitude, transmitting instructions to reduce an activity level, transmitting instructions to measure one of blood pressure or glucose, transmitting instructions to enter a response or other information for transmission back to the central monitoring system.

The information designed to instruct the monitored individual can also include information associated with the medical condition, information designed to confirm receipt of the received information, or information associated with treatment of the medical condition. For example, an image of a medication to treat the medical condition can be transmitted.

The information designed to instruct the monitored individual can be transmitted periodically. The period can change between transmissions based on the received information. The information can also be transmitted in response to an event identified in the received information.

In another aspect, a method performed by a medical condition sensing device associated with a monitored individual can include measuring a physiological condition of the monitored individual, transmitting the measured physiological condition to a central monitoring system, and receiving information designed to instruct the monitored individual from the central monitoring system. The received information can be based at least in part on the measured physiological condition.

This and other aspects can include one or more of the following features. The information designed to instruct the monitored individual can include instructions to undertake a predetermined action. The instructions to undertake a predetermined action can include, e.g., instructions to take medicine, instructions to contact a doctor, instructions to sit down, instructions to reduce altitude, instructions to reduce an activity level, instructions to measure one of blood pressure or glucose, instructions to enter a response or other information for transmission back to the central monitoring system.

The information designed to instruct the monitored individual can include information associated with the medical condition, information designed to confirm receipt of the received information, or information associated with treatment of the medical condition. For example, an image of a medication to treat the medical condition can be received.

The information designed to instruct the monitored individual can be received periodically. The period can change between transmissions based at least in part on the transmitted physiological condition. The information designed to instruct the monitored individual can be received in response to an event identified in the transmitted physiological condition.

The details of one or more implementations are set forth in the accompanying drawings and the description below. Other features will be apparent from the description and drawings, and from the claims.

DESCRIPTION OF DRAWINGS

FIG. 1 is a flow diagram of a method of controlling access to a medical monitoring device and/or an associated service.

Like reference symbols in the various drawings indicate like elements.

DETAILED DESCRIPTION

FIG. 1 depicts a flow diagram of a method of controlling access to a medical monitoring device and/or service. A medical monitoring device and its associated system are provided (20). The medical monitoring device and medical monitoring system may be of any operable type, such as that disclosed in U.S. Pat. No. 5,959,529 (hereafter, "the '529 patent"), whose disclosure is incorporated in its entirety, and/or modified as discussed herein.

Figure 2A:
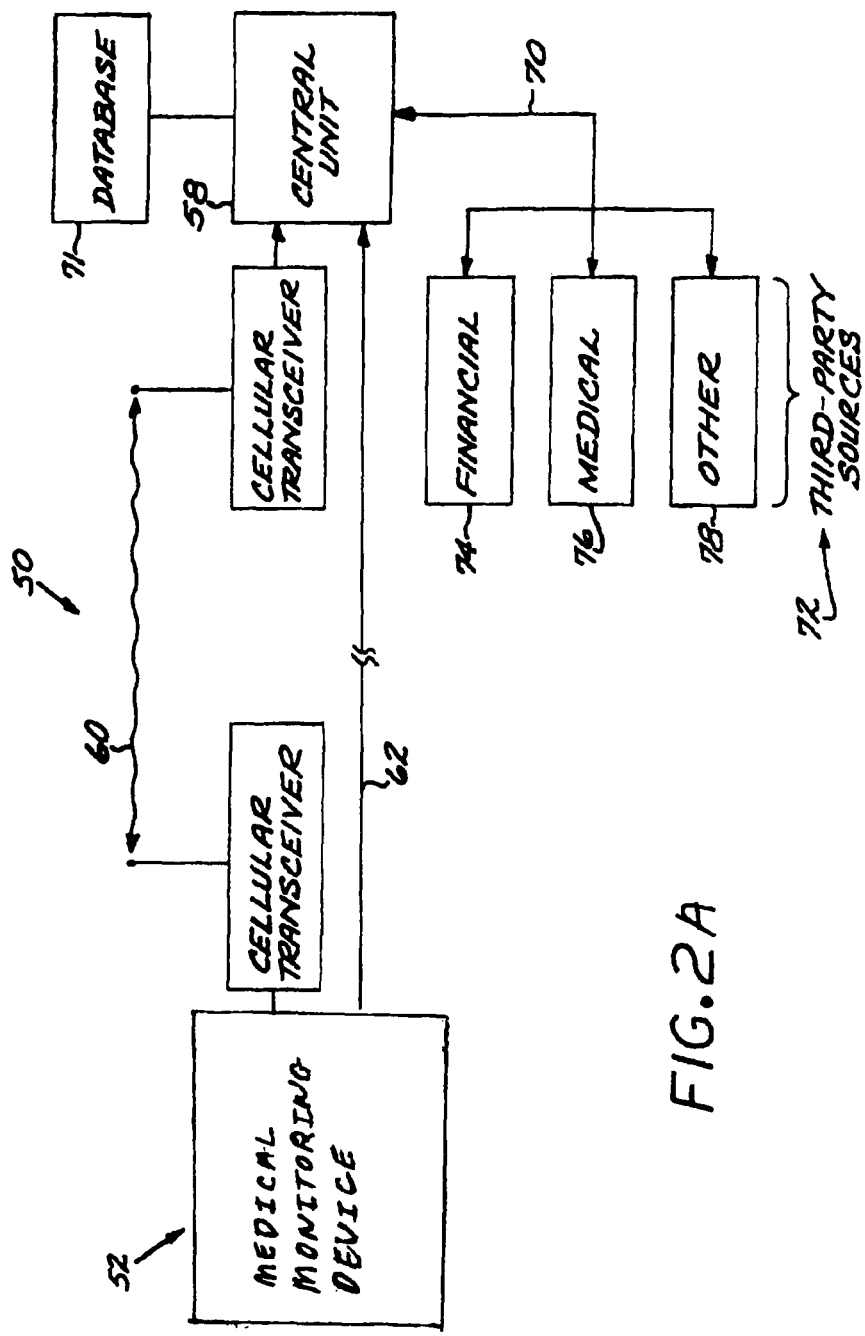
FIGS. 2A and 2B are schematic illustrations of medical monitoring systems for implementing the method of FIG. 1.
Figure 2B:
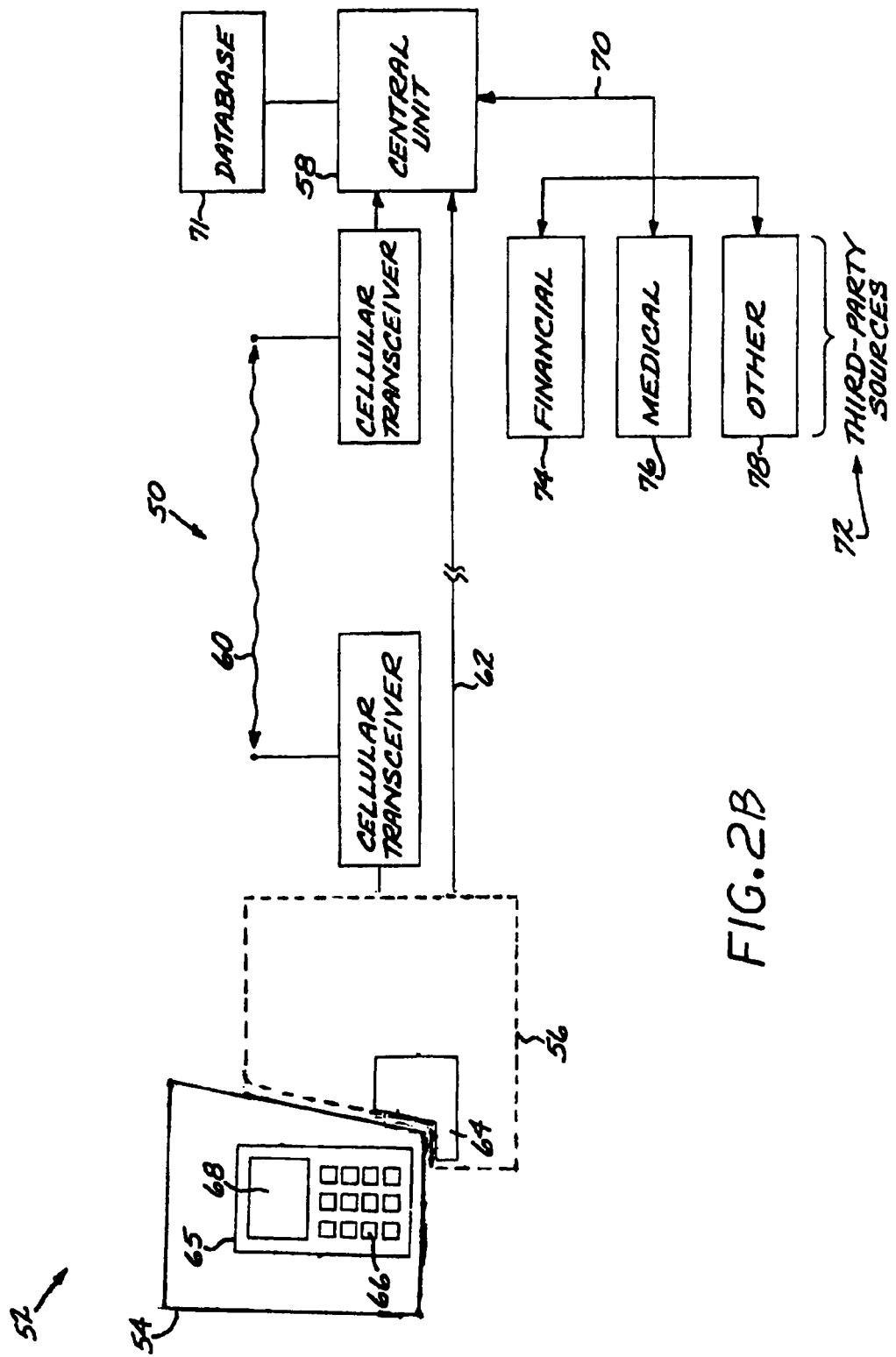

FIGS. 2A and 2B depict details, in block diagram form, of medical monitoring systems 50 that include a medical monitoring device system 52. Medical monitoring device systems 52 include one or more medical monitoring devices that monitor a biological parameter. A biological parameter is a quantity that characterizes an aspect of a biological system. In the medical context, biological parameters generally include information relating to the physiological state of an organism. Examples of medical monitoring devices include devices that measure electrical potentials (e.g., electrocardiography (ECG's), electromyography, and electroencephalography devices), devices that measure blood and other body fluid analyte constituents (e.g., pulse oximetry devices and devices that measure blood glucose concentration, blood pH, and/or other ion concentrations), and devices that measure mechanical characteristics (e.g., blood pressure transducers, heart sound transducers, height and/or weight measurement devices).

In FIG. 2B, medical monitoring device system 52 includes both a medical monitoring device 54 and a base station 56. The medical monitoring device 54 may be a portable or remote monitoring unit of the type generally described in the '529 patent. The base station 56 has communication access to a central unit 58 through a communication link such as a wireless cellular telephone transceiver link 60 and/or a telephone land-line 62. Alternatively, or in addition, communication links can be established by other available means, among others, such as wired or wireless networks that implement communications protocols and standards such IP (Internet protocol), WiFi (IEEE 802.11x), WiMax (IEEE 802.16x), and GPRS (General Packet Radio Service). The central unit 58, typically maintained at a central node or location, may in practice be composed of multiple computer systems distributed across, or even outside of, the central node.

In other implementations, medical monitoring device 54 can have direct communication access to central unit 58 through a communication link. For example, medical monitoring device 54 can include a cellular transceiver to establish a direct wireless cellular telephone transceiver link to central unit 58.

In the implementation shown in FIG. 2B, the base station 56 has a base station cradle 64 that is configured to receive the medical monitoring device 54. The medical monitoring device 54 includes an input/output device 65 that typically has a microprocessor, communications controller, and communications hardware and/or software to establish the links 60 and/or 62. The input/output device 65 has a keypad 66 for inputting information and a display 68 to view the input information and other information to be displayed, as well as information transmitted to the input/output device 65. Alternatively, input/output device 65 can use a touch-sensitive display without dedicated keys to interact with a user.

In the implementations shown in FIGS. 2A and 2B, the central unit 58 has communications access to a variety of databases 71 and to third-party sources 72, typically by telephone land-line, network or other connection 70. The databases 71 may include prior patient records, general records, and the like. The third-party sources 72 may include, for example, financial sources 74, medical sources 76, and other sources 78. A financial source might be, for example, an insurance company, the social-security administration, or a credit-granting company. A medical source might be, for example, a specialist physician whose authorization is required before commencing the monitoring of the patient. Other third-party sources might be, for example, the company that maintains the medical monitoring device and which is consulted to be certain that the specific medical monitoring device to be activated is approved for service.

In the implementation shown in FIG. 2B, the base station 56, when not prescribed or otherwise assigned and distributed to a patient to be monitored, ordinarily is in the custody the office of the agency that is providing the medical monitoring device 54 to a patient for the purpose of monitoring physiological parameters of the patient. Such an agency could be, for example, the patient's physician or a hospital. When the agency undertakes to provide the medical monitoring device 54 to the patient, for example, to take home, the medical monitoring device 54 is docked with the base station 56, and the procedures described in relation to subsequent portions of FIG. 1 are followed.

Returning to FIG. 1, a set of identification data elements (22) are input into the medical monitoring device system 52. For example, a set of identification data elements can be input through the keypad 66 of the input/output device 65 of the medical monitoring device 54 of FIG. 2B. The identification data elements may include, for example, one or more of a patient name, a patient address, a patient social security number, a patient sex, and an identification of the third-party financial source. In one implementation, a set-up sequence may involve the input of a patient number or other patient identifier. The input patient identifier can be used to retrieve other information about the patient, including name, address, social security number, sex, and the identity of a third-party financial source. The identifier of the medical monitoring device 54, such as its serial number, may be manually input in step 22, but more typically the identifier is automatically made available by the medical monitoring device 54 to the base station 56.

The input/output device 65 may perform a preliminary evaluation of the set of identification data elements, for example, such as to determine by using a software utility program whether the identification data elements meet a set of one or more format requirements. Such basic format requirements may be specified for each of the identification data elements. For example, a format requirement may specify that a patient name is to include only alphanumeric characters. If as typed into the keyboard the patient name includes other characters (e. g., a percent sign %), software running in the input/output device 65 can recognize the error and provide an input diagnostic message through the display 68 to prompt the input of correct information. In another example, a format requirement may specify that a user's social security number must contain 10 numerical digits and may not contain letters or other characters.

After what appears from the preliminary format evaluation to be a set of correct identification data elements is input to the input/output device 65, the medical monitoring device system 52 establishes (24) a communication link to the central unit 58. The communication link is preferably through the land-line 62, but may be though the cellular telephone transmission link 60 or another wireless or wired link if the land-line is not available.

The medical monitoring device system 52 and the central unit 58 cooperatively determine whether the medical monitoring device may be activated for rendering medical monitoring device service (26). The final decision is typically made by the central unit 58, although the medical monitoring device system 52 may aid in data processing or may be called upon for additional input, for example, such as when the patient name is found not to match with the social security number in other records.

The activation determination process 26 may include various sub-processes including evaluating the set of identification data elements as to whether they meet a set of basic structural requirements (28) and obtaining third-party authorization (30) from one or more of the third-party sources 72. The sub-processes of evaluating 28 and obtaining 30 are preferably performed automatically. "Automatically" as used herein indicates that the steps are performed without human action or intervention, except where a discrepancy occurs. The present system is organized to perform the evaluating and obtaining steps entirely by computer procedures, to minimize costs and take advantage of data collections at a variety of locations. Alternatively, the present approach may be performed in whole or in part using manual (i.e., human-performed) sub-processes 28 and 30. In addition, the sub-process 30 of obtaining third-party authorization can be performed either before or during the activation determination process 26. For example, the sub-process 30 may involve updating a locally stored (e.g., at a central unit hosting the medical monitoring service) copy of a third party's database of authorization information, and then performing the sub-process 30 by accessing the local copy of the database instead of accessing the third party's system, which typically would be maintained at a remote location. Updating of the local third-party authorization database may occur based on one or both of the following criteria: (i) periodically (e.g., once a day) or (ii) based on an occurrence of a predetermined event (e.g., the third-party system determines that a certain amount of new authorization data is available and has not yet been copied to the central unit's local database and/or the central unit determines that its local database does not contain needed information).

The set of basic structural requirements to be imposed may include the format requirements evaluated by the input/output device 65, or may include different or additional structural requirements. For example, the central unit 58 may check the database 71 to attempt to match the input patient name with a social security number that is already in the database 71 from prior medical contacts. If the patient name and the social security number that were input in sub-process 22 do not match, then further inquiry may be made back to the medical monitoring device system 52. The failure to match the name and the social security number may arise from a simple inputting error, which can be corrected with revised input, or it may arise from a fraudulent attempt to obtain medical monitoring services that is detected by the procedures of sub-process 28.

As noted above, obtaining third-party authorization in sub-process 30 may include contacting appropriate third-party sources 72, e.g., either on a dynamic, as-needed basis, and/or ahead of time by periodically replicating a third party's remote database to create a local copy. The financial source 74 may be contacted to determine whether it authorizes the charges associated with the patient monitoring services. This authorization is particularly important for the business interests of the provider of the services, for example, to avoid unpaid billings. Unpaid billings for medical services represents a major loss for many medical service companies. The medical source 76 may be contacted to determine whether it authorizes the patient monitoring. For example, if the prospective patient is being treated by more than one physician, it may be important to obtain authorization from each physician who is treating the patient before medical monitoring services are commenced. In this case, "authorization" signals formal recognition by the authorizing party that monitoring information will be available. Other sources 78 may also be contacted to determine whether they authorize the patient monitoring. For example, it may be desirable to ensure that the company responsible for maintaining a specific medical monitoring device authorizes its use. If a prior user had reported a problem and the specific medical monitoring device had been taken out of service for repair, but was mistakenly to be re-activated without being repaired, the company responsible for the maintenance could prevent its activation at this stage.

Thus, the procedures in sub-process 26 act as a "sign off" by a number of checks and third-parties to minimize the possibility that a medical monitoring device will be wrongly issued to a patient and activated. If the sign-offs are not completed, the medical monitoring device is not activated until the reason for the non-completion may be investigated. It is expected that in the great majority of cases, the activation determination process 26 will be completed without incident and so rapidly that the checking will be transparent to the patient and the issuer of the medical monitoring device.

Based on results of the activation determination process, the activation decision is made (32). The final decision is typically made at the central unit 58, although all or part of the final decision could be made at the base station and/or distributed or made by a system at another location. Typically, the decision is made at the central unit 58 because it has the access to the required information during the activation determination process 26, and because the central unit 58 tends to be more immune to tampering than the input/output device 65.

In the event that the identification data elements meet the set of basic structural requirements and third-party authorization is obtained, the central unit 58 issues an activation signal (34) to the medical monitoring device system 52 over the communication link 60 or 62. The medical monitoring device is activated and enters service (36).

The "activation signal" may be of any operable type. It may be a software "on" switch that enables the processing of data within a microprocessor in the medical monitoring device or a hardware "on" switch that turns on particular hardware functions such as the communications links built into the medical monitoring device. The activation signal may be complex, and may include identification of the patient and the specific medical monitoring device that is associated with that patient. This activation signal may then be transmitted with each subsequent communication between the medical monitoring device and the central unit 58 for identification purposes. In the event that the proper activation signal is not transmitted with each communication, it may be ignored. The activation may be revoked (38) at a later time if the authorization is withdrawn or for other reasons. Upon revocation 38, the signals transmitted by the medical monitoring device are not acted upon, and the patient and/or the issuing authority are notified and requested to return the medical monitoring device. As an alternative to revocation 38, the activation signal of step 34 may include a maximum time limit for which activation is authorized, so that a further authorization is required to extend the period of authorized use.

Figure 3:
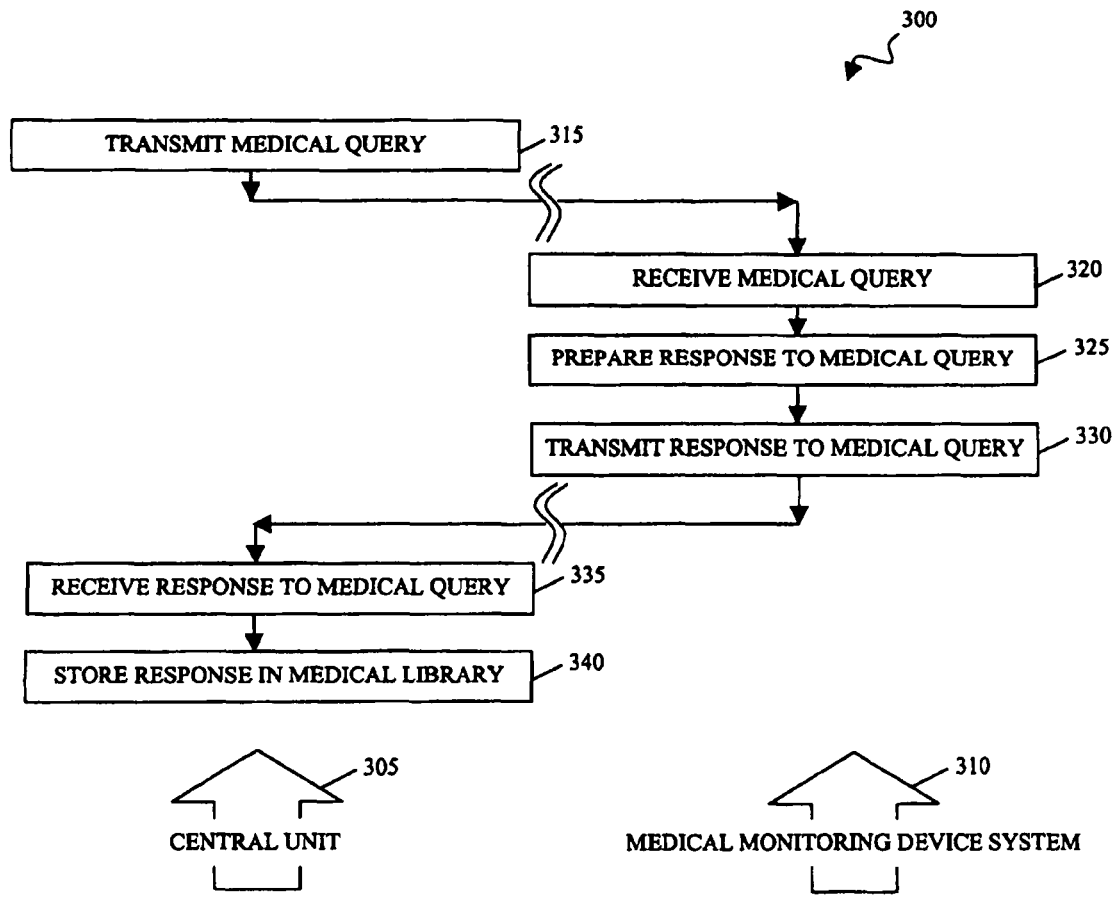
FIG. 3 is a flowchart of a process that can be performed by a medical monitoring device system during its term of service.

FIG. 3 shows a process 300 that can be performed during the term of service of a medical monitoring device. Aspects of process 300 performed by a central unit such as central unit 58 are denoted by arrow 305, whereas aspects of process 300 performed by a medical monitoring device such as device 54 are denoted by arrow 310. In process 300, a central unit sends a medical query to a medical monitoring device system at 315. A medical query is an inquiry regarding the medical condition of an individual who is monitored by a medical monitoring device.

Figure 4:
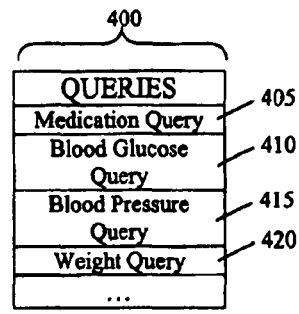
FIG. 4 shows a table of example medical queries that can be handled during the term of service of a medical monitoring device.

FIG. 4 shows a table 400 that identifies example medical queries 405, 410, 415, 420. Medical query 405 is an inquiry regarding the medication of an individual. For example, medical query 405 can inquire whether or not the individual has recently medicated with a particular medication or medical query 405 can inquire as to the dosage at which the individual has medicated. Medical query 410 is an inquiry regarding the individual's blood glucose concentration. Medical query 415 is an inquiry regarding the individual's blood pressure. Medical query 420 is an inquiry regarding the individual's weight.

Medical queries can be patient-specific in that they are relevant to the medical state of an individual or to classes of individuals. Medical queries can be tailored to the individual's medical condition, location, or activities. Medical queries can address a number of different disease states, including those outside the purview of the primary function of the medical monitoring device system. For example, when the medical monitoring device system is an electrocardiograph, medical queries can include queries directed to an individual's diabetic condition.

In addition, medical queries can be periodic queries made at certain fixed intervals during the monitoring of an individual. For example, periodic queries as to an individual's blood pressure can be made every four hours or so, whereas periodic queries as to an individual's weight can be made every three months or so. Medical queries can also be "one time" queries in that they are made during the onset of monitoring. Such queries can inquire as to the individual's age, gender, and medical history. Medical queries can also be "dynamic" queries in that the frequency at which the queries are made is adjusted based on the responses to previous queries or the responses to previous activity prompts, as discussed below. For example, when a response to a blood glucose query 410 indicates that the individual's blood glucose level is falling, the frequency of subsequent blood glucose queries 410 can be increased until the individual's blood glucose level ceases to fall or begins to increase.

Returning to FIG. 3, the transmitted medical query is received at a medical monitoring device at 320. The medical query can be received over a wireless communication link and/or a wired communication link. The medical monitoring device can then prepare a response to the received medical query at 325. The preparation of the response can be performed automatically, i.e., without input from the individual who is monitored. For example, the response can be prepared using monitoring results read from a sensor. Alternatively, the response can be prepared based on input from the individual who is monitored. For example, the medical monitoring device system can present a text version of the medical query to the monitored individual. The medical monitoring device system can then receive information used to frame a response over one or more input devices.

Once the response is prepared, the medical monitoring device can transmit the prepared response to a central unit at 330. The response can be transmitted over a wireless communication link and/or a wired communication link. The central unit can receive the response to the medical query at 335. The received response can be stored in a medical library that includes other information relating to the medical condition of the monitored individual at 340. One implementation of such storage is discussed further below.

Figure 5:
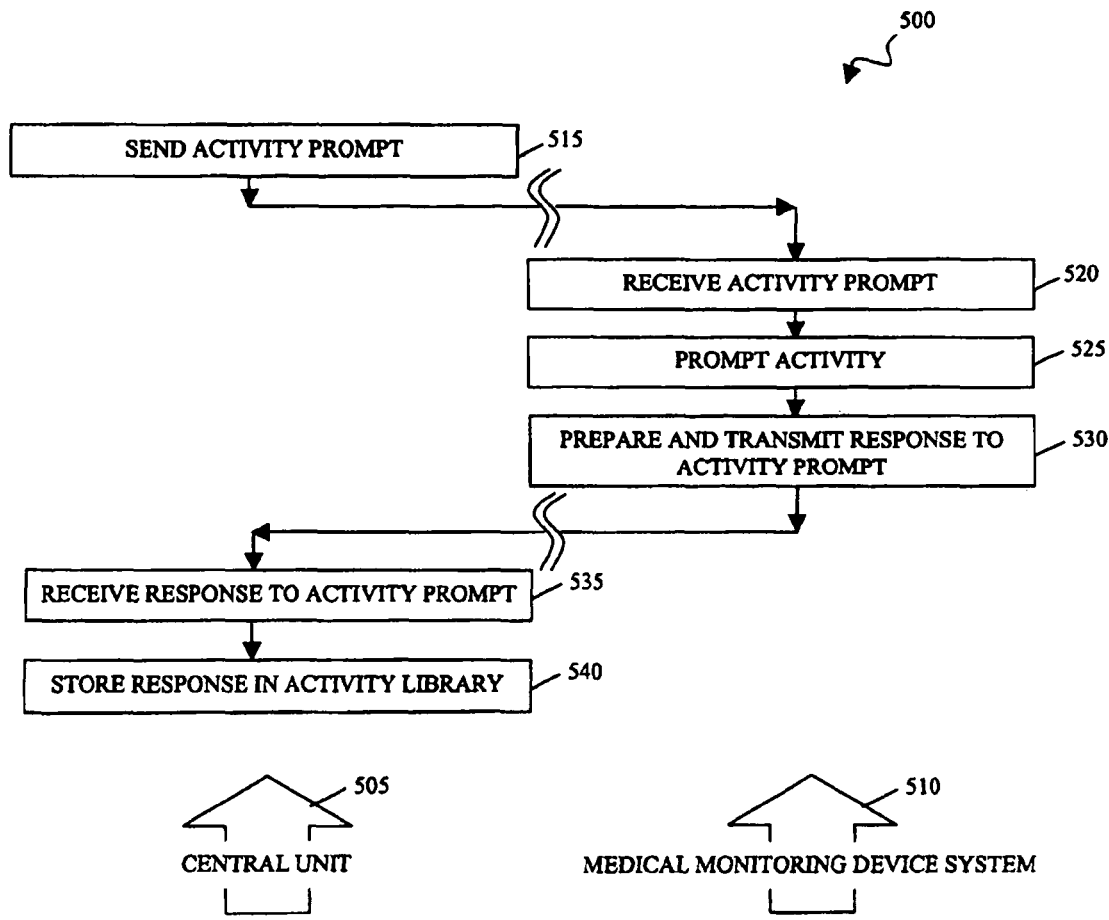
FIG. 5 is a flowchart of a process that can be performed by a medical monitoring device system during its term of service.

FIG. 5 shows a process 500 that can be performed during the term of service of a medical monitoring device system. Aspects of process 500 performed by a central unit such as central unit 58 are denoted by arrow 505, whereas aspects of process 500 performed by a medical monitoring device such as device 54 are denoted by arrow 510.

Figure 6:
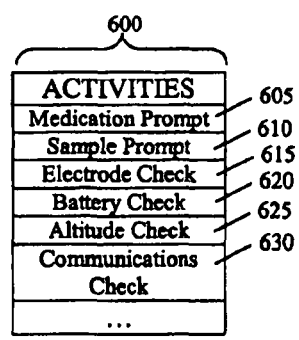
FIG. 6 shows a table of example activity prompts that can be handled during the term of service of a medical monitoring device.

In process 500, a central unit sends an activity prompt to a medical monitoring device at 515. An activity prompt is a trigger designed to provoke a particular action. FIG. 6 shows a table 600 that identifies example activity prompts 605, 610, 615, 620, 625, 630. Activity prompt 605 is a trigger designed to provoke a monitored individual to medicate in a certain way. For example, activity prompt 605 can identify a medication and a dosage for the medication that is to be taken by the monitored individual. The medication can be identified, e.g., by name, by ID #, by shape, or by color. Medication can also be identified using a visual display device that presents an image of the medication (e.g., a purple, ovoid capsule) to identify the medication. Activity prompt 610 is a trigger designed to provoke the collection of a sample. For example, activity prompt 610 can provoke a monitored individual to take a urine sample or a blood sample. Activity prompt 610 can also prompt an individual to facilitate monitoring using a medical monitoring device system. For example, when the medical monitoring device system is a electrocardiograph, activity prompt 610 can prompt the monitored individual to ensure that electrodes are connected, to minimize the amount or type of movement, or to recline for collection of an electrocardiograph signal sample.

Activity prompt 615 is a trigger designed to provoke a monitored individual to check that any electrodes of the medical monitoring device are deployed properly. For example, activity prompt 615 can provoke a monitored individual to check that contact between the monitoring electrodes and the proper portion of and/or location on the body is maintained. Activity prompt 620 is a trigger designed to provoke a monitored individual to check that a battery or other power source for the medical monitoring device is sufficiently charged to properly supply the medical monitoring device with power. Activity prompt 625 is a trigger designed to provoke a monitored individual to check and decrease his or her altitude. In particular, individuals with certain medical conditions may be respond unfavorably to altitudes and activity prompt 625 may act to remind them to consider altitude during activities. Activity prompt 630 is a trigger designed to provoke a monitored individual to consider the likelihood of losing one or more communications links with the central unit. For example, activity prompt 630 can be triggered when a signal over a wireless communication link is fading.

Activity prompts can also be patient-specific in that they are relevant to the monitored individual or to classes of individuals. Activity prompts can be tailored to the individual's medical condition, location, or activities. Activity prompts can address a number of different disease states, including those outside the purview of the primary function of the medical monitoring device system. For example, when the medical monitoring device system is an electrocardiograph, activity prompts can include queries directed to an individual's participation in a clinical trial, as discussed below.

Activity prompts can also be periodic in that they are made a certain fixed intervals during the monitoring of an individual. For example, periodic prompts to medicate can be made in accordance with an individual's medication regimen. Activity prompts can also be "one time" prompts in that they are made during the onset of monitoring. Activity prompts can also be "dynamic" prompts in that the frequency at which the prompt are made is adjusted based on the responses to previous prompts or the responses to previous queries. For example, when responses to altitude check prompts 625 consistently indicate that an individual is at or near sea level, the frequency of altitude check prompts 410 can be decreased until an anomalous response is obtained.

Additional examples of activity prompts include triggers designed to provoke a monitored individual to, e.g., lie down, sit down, curtail or halt physical activity, commence or increase physical activity, apply pressure to a wound, contact a doctor, call an ambulance, decrease altitude, measure blood glucose level, measure blood pressure, take a diuretic, or hydrate.

Returning to FIG. 5, the transmitted activity prompt is received at a medical monitoring device at 520. The activity prompt can be received over a wireless communication link and/or a wired communication link. The medical monitoring device can prompt the desired activity at 525. Such prompting can be directed to the monitored individual or to other elements in the medical monitoring device. In one implementation, a message is presented to the monitored individual over an output device such as an LCD screen. In another implementation, data collection elements in the medical monitoring device are directed to collect a certain sample.

The medical monitoring device can also prepare and transmit a response to the received activity prompt at 530. The preparation of the response can be done automatically, i.e., based on sensor readings and without input from the individual who is monitored. For example, when the medical monitoring device system is an electrocardiograph, the prepared response can include electrocardiogram data. Alternatively, the preparation of the response can be based on input from the individual who is monitored. For example, the medical monitoring device can present a text version of the activity prompt to the monitored individual and then receive a response over one or more input devices.

Once the response is prepared, the medical monitoring device system can transmit the prepared response to a central unit at 530. The response can be transmitted over a wireless communication link and/or a wired communication link. The central unit can receive the response to the activity prompt at 535. The received response can be stored in an activity library that includes other information relating to other activities of the monitored individual at 540.

Figure 7:
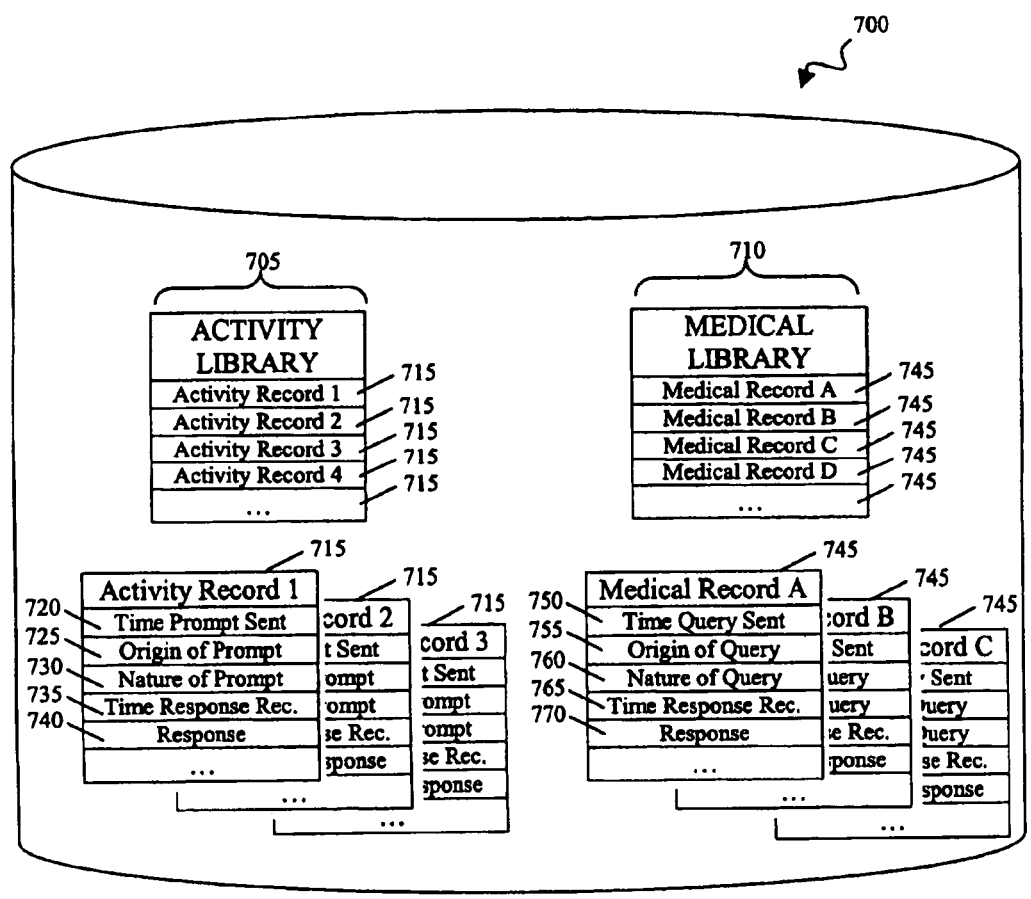
FIG. 7 shows a data store for storing information during the term of service of a medical monitoring device.

FIG. 7 shows a data store 700 suitable for storing one or more activity libraries 705 and one or more medical libraries 710. Activity library 705 includes a collection of activity records 715 that describe individual activities that have been prompted by the central unit. For example, each activity record 715 can include a time prompt sent field 720, a prompt origin field 725, a nature of prompt field 730, a time response received field 735, and a response field 740. Time prompt sent field 720 includes information identifying the time when the prompt was transmitted from the central unit to the medical monitoring device system. Prompt origin field 725 includes information identifying the cause of the prompt. For example, an altitude check prompt may be sent when a monitored condition at the medical monitoring device system indicates that altitude may be a factor in the medical condition of the monitored individual. The monitored condition can be, e.g., a geographic location identified using a global positioning satellite (GPS) reading taken by the device.

Nature of prompt field 730 includes information identifying the subject of the transmitted prompt. For example, nature of prompt field 730 can identify the activity that was designed to be triggered. Time response received field 735 can include information identifying the time when a response to the prompt was received. Response field 740 can include information identifying the response received. For example, response field 740 can identify that the monitored individual has taken the prompted medication or that the monitored individual has collected a biological sample.

Medical library 710 includes a collection of medical records 745 that describe responses to queries by the central unit. For example, each medical record 745 can include a time query sent field 750, a query origin field 755, a nature of query field 760, a time response received field 765, and a response field 770. Time query sent field 750 includes information identifying the time when the query was transmitted from the central unit to the medical monitoring device system. Query origin field 755 includes information identifying the cause of the query. For example, a query regarding the monitored individual's blood glucose level can be sent in response to the passage of a fixed period of time and a medication query may be sent in response to an anomalous measurement by the medical monitoring device system.

Nature of query field 760 includes information identifying the subject of the transmitted query. For example, nature of query field 760 can identify that the query is one or more of the queries in table 400 (FIG. 4). Time response received field 765 can include information identifying the time when any response to the query was received. Response field 770 can include information identifying the response received. For example, response field 770 can identify that the monitored individual is not medicated or that the monitored individual has a certain blood pressure.

Libraries 705, 710 can be implemented in virtually any sort of data repository including databases, data tables, linked lists, or other associations of records 715, 720. Records 715, 720 can be data objects, data records, or other associations of information. Associations between data in libraries 705, 710 and records 715, 720 can be formed using, e.g., directories, files, filenames, or pointers. Libraries 705, 710 and records 715, 720 can be stored in a single data storage device or libraries 705, 710 and records 715, 720 can distributed among two or more data storage devices.

Figure 8:
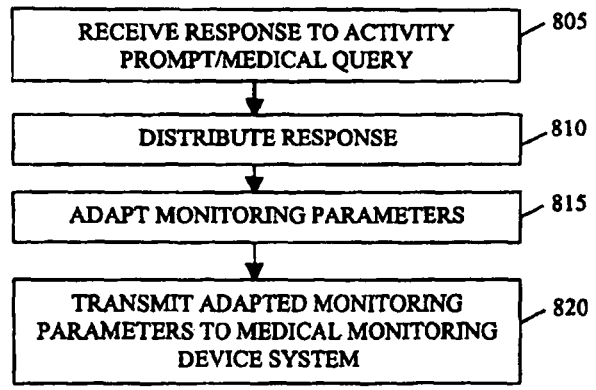
FIG. 8 is a flowchart of a process that can be performed by a central unit in response to receipt of information from a medical monitoring device system.

FIG. 8 shows a process 800 that can be performed by a central unit in response to receipt of a response to a medical query, receipt of a response to an activity prompt, or receipt of other information from a medical monitoring device system. For example, process 800 can be performed by central unit 58 (FIG. 2).

The system performing process 800 receives the response or other information at 805. The response can be received over a wired or a wireless data communications link.

In response to receipt of the response, the system can distribute the response to one or more third parties to whom the response is relevant at 810. For example, if the response indicates that a sample has been collected, the information regarding the collection can be distributed to a physician, a manager of a clinical trial, or other concerned party. In the case of sensor readings or other data samples, the distributed information can include the collected sample itself.

The system performing process 800 can also adapt the parameters of the monitoring performed by the medical monitoring device system at 815. The parameters can be adapted, e.g., to change thresholds at which disease states are identified, to change the algorithms used in monitoring, or to change the nature of the monitoring itself. The adaptation of the parameters can be based on the response or other information received from the medical monitoring device system or the adaptation can be based on input from the third party to whom the response or other information has been distributed.

After adapting the parameters of the monitoring, the system can transmit the adapted parameters to the medical monitoring device system at 820. The transmission can result in the medical monitoring device system adapting the monitoring to accord with the transmitted parameters.

Figure 9:
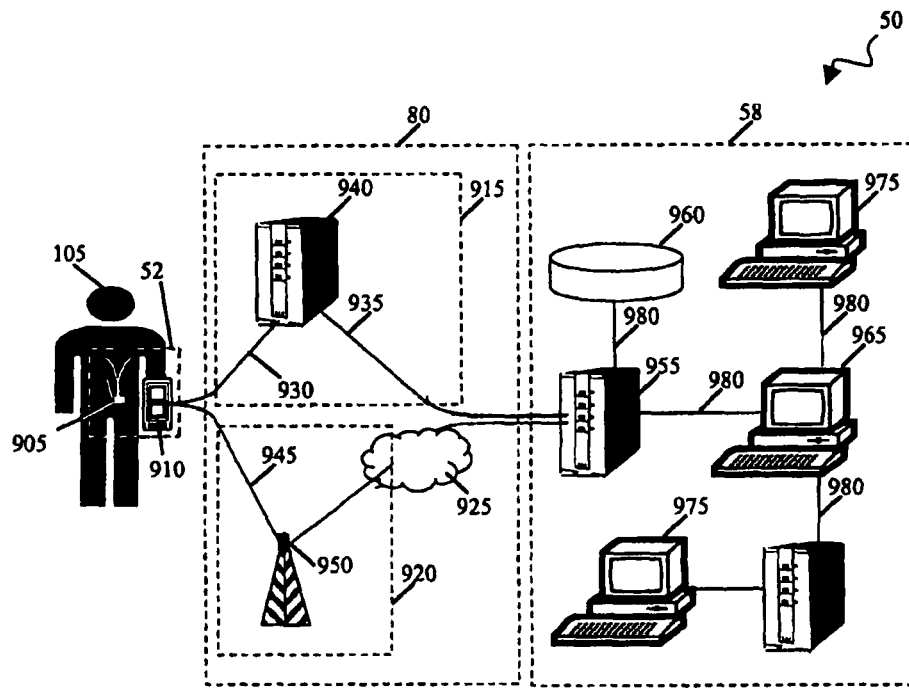
FIG. 9 is a schematic illustration of another implementation of a medical monitoring system.

FIG. 9 shows another implementation of a medical monitoring system 50 for monitoring an individual 105. Medical monitoring system 50 includes medical monitoring device system 52 in communication with central unit 58 over one or more communication links 80.

Medical monitoring device system 52 can be adapted for electrocardiographic monitoring of an individual 105. Medical monitoring device system 52 can include a sensor module 905 and a monitor module 910. Sensor module 905 can include three ECG leads with electrodes, as well as a two channel ECG signal recorder and a wireless and/or wired data output. Sensor module 905 can also include a clip for attaching sensor module to a belt, a neckpiece, or other item worn by individual 105. Monitor module 910 includes a data input that is adapted to receive data output from sensor module 905 as well as one or more wireless and/or wired data outputs for data communication over communication link 80. Monitor module 910 also includes a data processing device that performs data processing activities in accordance with the logic of a set of machine-readable instructions. The instructions can be realized in digital electronic circuitry, integrated circuitry, specially designed ASICs (application specific integrated circuits), computer hardware, firmware, software, and/or combinations thereof. The instructions can describe how to identify and/or handle electrocardiogram data in accordance with one or more of the techniques described herein. Monitor module 910 can also include an input device and an output device for interaction with a user. The output device can present a prompt or a query to the monitored individual. The input device can receive information used in framing a response to a presented prompt or query.

Communication link 80 can include one or both of a wired data link 915 and a wireless data link 920 coupled to a data network 925 to place medical monitoring device system 52 in data communication with central unit 58. Wired data link 915 includes a public network portion 930 and a private or virtual private network portion 935 bridged by a server 940. Public network portion 930 provides for data communication between medical monitoring device system 52 and server 940 over a wired data link such as a telephone network. Private network portion 935 provides for private or virtually private data communication from server 940 to receiver 120. Server 940 can interface for data communication with both portions 930, 935. For example, server 940 can communicate directly with central unit 58 using the peer-to-peer protocol (PPP).

Wireless data link 945 can include one or more wireless receivers and transmitters 950 such as a WiFi receiver, a cellular phone relay station, and/or other cellular telephone infrastructure to place medical monitoring device system 52 in data communication with data network 925. In turn, data network 925 communicates with central unit 58.

Central unit 58 includes a receiver server 955, a data storage device 960, a call router 965, a communications server 970, and one or more application servers 975 that are all in data communication with one another over one or more data links 980. Receiver server 955 is a data processing device that receives and transmits communications over communications link 80 and relays incoming communications to data storage device 960 and call router 965 in accordance with the logic of a set of machine-readable instructions. Data storage device 960 is a device adaptable for the storage of information. For example, data storage device 960 can store one or more activity libraries 705 and/or medical libraries 710 (FIG. 7). Data storage device 960 can be a volatile and/or non-volatile memory that records information electrically, mechanically, magnetically, and/or optically. Call router 965 is a data processing device that, in accordance with the logic of a set of machine-readable instructions, identifies the content of an incoming communication and directs the communication to one or more appropriate application servers 975 based on that content. Communications server 970 is a data processing device that relays communications between call router 965 and one or more application servers 975 over an external network. Application servers 975 are data processing devices that interact with a user or operate in isolation to provide one or more monitoring services in accordance with the logic of a set of machine-readable instructions. Data links 980 can be part of a local area and/or private network or part of a wide area and/or public network.

In operation, sensor module 905 can sense, amplify, and record electrical signals relating to the activity of the heart. Sensor module 905 can also relay all or a portion of those signals to monitor module 910 where they can be managed. For example, monitor module 910 can manage the signals in accordance with one or more of processes 300 and 500 (FIGS. 3 and 5). As part of the management, monitor module 910 can transmit the signals to central unit 58. The signals can be transmitted alone or in association with other information. For example, the signals can be transmitted in association with other information that is responsive to queries or prompts.

The transmitted signals pass along communications link 80 over one or more of wired data link 915 and wireless data link 920 to central unit 58. At central unit 58, the signals are received by server 955 which causes at least a portion of the incoming signals to be stored on data storage device 960 and relayed to call router 965. The incoming signals stored on data storage device 960 can be stored any of a number of data structures The incoming signals relayed to call router 965 can be distributed to one or more appropriate application servers 975. The distribution can be based on one or more different factors, including the load on certain application servers 975, the resources available at certain application servers 975 (e.g., the amount and/or type of memory available), or the content of the incoming signals. For example, when the signal relates to a certain category of cardiac event, the signal can be distributed to a certain application server 975 that is accessible to a cardiologist having expertise with that certain category of event. As another example, when the signal originates with an individual who is under the care of a particular physician, the signal can be distributed to a certain application server 975 that is accessible to that physician. As yet another example, when the signal relates to a certain category of cardiac event, the signal can be directed to a certain application server 975 that accesses an expert system or other set of instructions for diagnosing and/or treating that category of event. When appropriate, a signal can be routed to communications server 970 which in turn relays the signal to the appropriate application server 975 over an external network.

Communications can also be transmitted from central unit 58 back to individual 105 or to other individuals, as discussed above. As yet another example, when a physician or expert system identifies that care is needed, a message requesting that the individual seek care can be returned to individual 105 over communication link 80. In urgent care situations, third parties such as medical personnel can be directed to individual 105 by medical monitoring device system 52.

Figure 10:
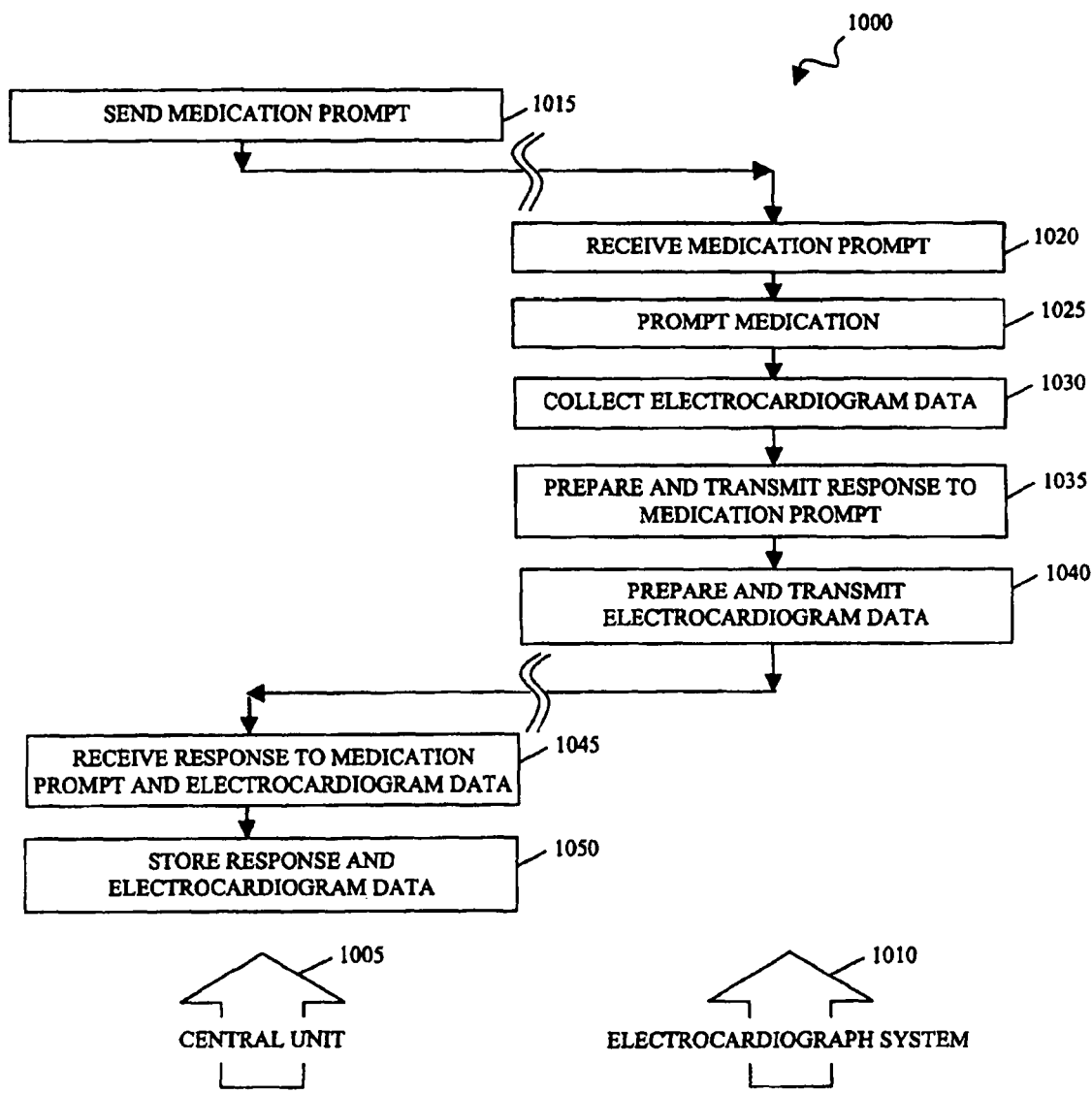
FIG. 10 is a flowchart of a process that can be performed by a electrocardiograph monitoring system during a clinical trial.

FIG. 10 shows a process 1000 that can be performed using an electrocardiographic monitoring device during a clinical trial. A clinical trial is an experiment involving a set of human subjects having a clinical event as an outcome measure. Clinical trials are generally designed to yield information about the efficacy or safety of a drug, vaccine, diagnostic test, surgical procedure, or other medical intervention. For the sake of convenience, such interventions are referred to herein as "medication."

Aspects of process 1000 performed by a central unit such as central unit 58 are denoted by arrow 1005, whereas aspects of process 1000 performed by an electrocardiographic monitoring device are denoted by arrow 1010.

In process 1000, a central unit sends a medication prompt to an electrocardiograph system at 1015. The medication prompt is designed to trigger the monitored individual to medicate in accordance with the guidelines of the clinical trial. For example, the medication prompt can prompt the monitored individual to take a specified dosage of a specified pharmaceutical composition at a specified time. The medication prompt can be tailored to the monitored individual and based on factors such as the individual's weight, activity level, age, and medical history. The prompted medication need not be thought to have a direct consequence on cardiac function, but rather the prompted medication can be suspected of having a minimal effect or of having no effect on cardiac activity.

The transmitted medication prompt is received at the electrocardiogram system at 1020. The electrocardiogram system can then prompt the appropriate medication at 1025. For example, the electrocardiogram system can direct the monitored individual to dose with a specific medication in accordance with the clinical trial. The electrocardiogram system can collect electrocardiogram data before and after the dosage at 1030 as part of the clinical trial.

The medical monitoring device can also prepare and transmit a response to the medication prompt at 1035. The preparation of the response can be done automatically, i.e., without input from the individual who is monitored. Alternatively, the preparation of the response can be based on input from the individual who is monitored. For example, the medical monitoring device can present a text version of the medication prompt to the monitored individual and then receive a confirmation that the monitored individual has medicated as instructed.

The medical monitoring device can also prepare and transmit electrocardiogram data to the central unit at 1040. The transmitted data can be raw or processed data. The transmitted data can correspond to specific cardiac events of clinical significance or the transmitted data can correspond to a representative sample of the electrocardiogram data.

The central unit can receive the electrocardiogram data and the response to the medication prompt at 1045. The received data and response can be stored at 1050 and used to yield information about the efficacy or safety of the medication in the context of the clinical trial.

A number of implementations have been described. Nevertheless, it will be understood that various modifications may be made. Accordingly, other implementations are within the scope of the following claims.

What is claimed is:

1. A method for transmitting instructions from a central monitoring system to a patient-portable physiological condition-sensing device associated with a monitored individual, the method comprising:
   receiving information indicating that the sensing device seeks access to the central monitoring system;
   receiving, from a financial third-party source, financial authorization data comprising an authorization for the monitored individual to utilize the patient-portable physiological condition-sensing device;
   determining whether the sensing device is authorized to access the central monitoring system, the determination being based at least in part on the financial authorization data received from the financial third-party source;
   based on the result of the determination, transmitting, from the central monitoring system, a first instruction designed to instruct at least one of the sensing device and the monitored individual to measure a first physiological condition of the monitored individual, wherein the first instruction comprises a text version of the first instruction presented to the monitored individual;
   measuring, by the sensing device, the instructed measurement of the first physiological condition;
   receiving, at the central monitoring system from the sensing device, the instructed measurement of the first physiological condition;
   a first length of time after transmitting the first instruction, transmitting from the central monitoring system to the sensing device, a second instruction designed to instruct at least one of the sensing device and the monitored individual to measure a second physiological condition of the monitored individual;
   measuring, by the sensing device, the instructed measurement of the second physiological condition; and
   receiving, at the central monitoring system from the sensing device, the instructed measurement of the second physiological condition.

2. The method of claim 1, further comprising receiving instructions designed to instruct the monitored individual to check a charge of a battery associated with the patient-portable physiological condition-sensing device.

3. The method of claim 1, further comprising processing the measurements of the first physiological condition, by the patient-portable physiological condition-sensing device, prior to transmitting the measurement of the first physiological condition to the central monitoring system.

4. The method of claim 1, wherein at least one of the transmitting and the receiving uses a wireless communication link.

5. The method of claim 1, wherein the first length of time is based on whether the measurement of the first physiological condition from the sensing device contains an anomalous measurement.

6. The method of claim 1, further comprising the step of transmitting a query to the financial third-party source for the financial authorization data.

7. The method of claim 1, further comprising the step of receiving, from a medical third-party source, medical authorization data comprising an authorization for the monitored individual to utilize the sensing device, wherein determining whether the sensing device is authorized to access the central monitoring system is based at least in part on the medical authorization data received from the medical third-party source.

8. The method of claim 1, further comprising the step of receiving, from a medical device third-party source, medical device authorization data comprising an authorization for the monitored individual to utilize the sensing device, wherein determining whether the sensing device is authorized to access the central monitoring system is based at least in part on the medical device authorization data received from the medical device third-party source.

9. A system for transmitting instructions, comprising:
a patient-portable physiological condition-sensing device associated with a monitored individual, the sensing device comprising a sensor measuring a physiological condition of the monitored individual;
a central monitoring system, the central monitoring system comprising data processing circuitry, and further comprising a communications link configured to:
receive, from a financial third-party source, financial authorization data comprising an authorization for the monitored individual to utilize the sensing device;
receive information indicating that the sensing device seeks access to the central monitoring system;
transmit a first instruction designed to instruct at least one of the sensing device and the monitored individual to measure a first physiological condition of the monitored individual, wherein the first instruction comprises a text version of the first instruction presented to the monitored individual;
receive the instructed measurement of the first physiological condition from the sensing device;
transmit a second instruction designed to instruct at least one of the sensing device and the monitored individual to measure a second physiological condition of the monitored individual; and
receive, from the sensing device, the instructed measurement of the second physiological condition;
wherein the data processing circuitry is configured to:
determine whether the sensing device is authorized to access the central monitoring system, the determination being based at least in part on the financial authorization data received from the financial third-party source;
based on the result of the determination, generate, for transmission by the communications link, the first instruction; and
a first length of time after transmitting the first instruction, generate, for transmission to the sensing device by the communications link, the second instruction.

10. The system of claim 9, wherein the communications link is further configured to transmit a query to the financial third-party source for the financial authorization data.

11. The system of claim 9, wherein the communications link is further configured to receive, from a medical third-party source, medical authorization data comprising an authorization for the monitored individual to utilize the sensing device, and wherein the determination that the sensing device is authorized to access the central monitoring system is further based at least in part on the medical authorization data received from the medical third-party source.

12. The system of claim 9, wherein the communications link is further configured to receive, from a medical device third-party source, medical device authorization data comprising an authorization for the monitored individual to utilize the sensing device, and wherein the determination that the sensing device is authorized to access the central monitoring system is further based at least in part on the medical device authorization data received from the medical device third-party source.

* * * * *